(12) United States Patent
McCusker et al.

(10) Patent No.: US 7,723,551 B2
(45) Date of Patent: May 25, 2010

(54) PROCESS FOR THE SIMULTANEOUS CO-PRODUCTION OF 2,2,4,4-TETRAMETHYLCYCLOBUTANE-1,3-DIOL AND 1,4-CYCLOHEXANEDIMETHANOL

(75) Inventors: Jennifer Ellen McCusker, Kingsport, TN (US); Jerome Leonard Stavinoha, Jr., Longview, TX (US); Christopher Fletcher Tomlin, Kingsport, TN (US); Michael Wayne Salyer, Kingsport, TX (US)

(73) Assignee: Eastman Chemical Company, Kingsport, TN (US)

( * ) Notice: Subject to any disclaimer, the term of this patent is extended or adjusted under 35 U.S.C. 154(b) by 87 days.

(21) Appl. No.: 11/948,032

(22) Filed: Nov. 30, 2007

(65) Prior Publication Data

US 2008/0154012 A1 Jun. 26, 2008

Related U.S. Application Data

(60) Provisional application No. 60/872,379, filed on Dec. 2, 2006.

(51) Int. Cl.
*C07C 35/04* (2006.01)
(52) U.S. Cl. .................................................. 568/839
(58) Field of Classification Search .................. 568/839
See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,806,064 A | 9/1957 | McIlveen | |
| 2,936,324 A | 5/1960 | Hasek et al. | |
| 3,000,906 A | 9/1961 | Hasek et al. | |
| 3,190,928 A | 6/1965 | Elam et al. | |
| 3,201,474 A | 8/1965 | Hasek et al. | |
| 3,227,764 A | 1/1966 | Martin et al. | |
| 3,236,899 A | 2/1966 | Clark et al. | |
| 3,259,469 A | 7/1966 | Painter et al. | |
| 3,287,390 A | 11/1966 | Poos et al. | |
| 3,288,854 A | 11/1966 | Martin et al. | |
| 3,312,741 A | 4/1967 | Martin et al. | |
| 3,329,722 A | 7/1967 | Rylander | |
| 3,366,689 A | 1/1968 | Maeda et al. | |
| 3,403,181 A | 9/1968 | Painter et al. | |
| 5,118,847 A | 6/1992 | Jackson et al. | |
| 5,169,994 A | 12/1992 | Sumner et al. | |
| 5,258,556 A * | 11/1993 | Sumner et al. | 568/839 |
| 5,475,144 A | 12/1995 | Watson et al. | |
| 6,232,504 B1 | 5/2001 | Barteau et al. | |
| 6,919,489 B1 * | 7/2005 | McCusker-Orth | 568/864 |

OTHER PUBLICATIONS

USPTO Office Action dated Apr. 1, 2008 for co-pending U.S. Appl. No. 11/948,000.
USPTO Office Action dated Apr. 1, 2008 for co-pending U.S. Appl. No. 11/948,047.
USPTO Office Action dated Jun. 25, 2008 for co-pending U.S. Appl. No. 11/947,981.
Co-Pending U.S. Appl. No. 11/948,000, filed Nov. 30, 2007, Jennifer Ellen Mccusker-Orth, et al.
Co-Pending U.S. Appl. No. 11/948,047, filed Nov. 30, 2007, Jennifer Ellen Mccusker-Orth, et al.
Co-Pending U.S. Appl. No. 11/947,981, filed Nov. 30, 2007, Jennifer Ellen Mccusker-Orth, et al.
Co-Pending U.S. Appl. No. 11/947,941, filed Nov. 30, 2007, Jennifer Ellen Mccusker-Orth, et al.
Co-Pending U.S. Appl. No. 11/947,950, filed Nov. 30, 2007, Jennifer Ellen Mccusker-Orth, et al.

* cited by examiner

*Primary Examiner*—Brian J Davis
(74) *Attorney, Agent, or Firm*—Louis N. Moreno; Bernard J. Graves, Jr.

(57) ABSTRACT

The present disclosure pertains to processes for the simultaneous co-production of 2,2,4,4-tetramethylcyclobutane-1,3-diol and 1,4-cyclohexanedimethanol by hydrogenation 2,2,4,4-tetramethylcyclobutane-1,3-dione and dimethylcyclohexane-1,4-dicarboxylate, respectively, under hydrogenation conditions of temperature and pressure.

26 Claims, No Drawings

PROCESS FOR THE SIMULTANEOUS CO-PRODUCTION OF 2,2,4,4-TETRAMETHYLCYCLOBUTANE-1,3-DIOL AND 1,4-CYCLOHEXANEDIMETHANOL

CROSS REFERENCES TO RELATED APPLICATIONS

This application claims priority under 35 U.S.C. §119(e) to U.S. Provisional Application Ser. No. 60/872,379 filed on Dec. 2, 2006, which is hereby incorporated by reference.

FIELD OF THE INVENTION

The present disclosure relates to the simultaneous co-production of 2,2,4,4-tetramethylcyclobutane-1,3-diol and 1,4-cyclohexanedimethanol. In one embodiment, the present invention relates to the simultaneous co-production of 2,2,4,4-tetramethylcyclobutane-1,3-diol and 1,4-cyclohexanedimethanol by hydrogenation of 2,2,4,4-tetramethylcyclobutane-1,3-dione and dimethylcyclohexane-1,4-dicarboxylate, respectively, in the presence of a copper-based catalyst.

BACKGROUND OF THE INVENTION 2,2,4,4-Tetramethylcyclobutane-1,3-diol is an important intermediate for producing a variety of polymeric materials having advantageous properties. 2,2,4,4-Tetramethylcyclobutane-1,3-diol is typically produced by the catalytic hydrogenation of the corresponding 2,2,4,4-tetramethylcyclobutane-1,3-dione as shown below.

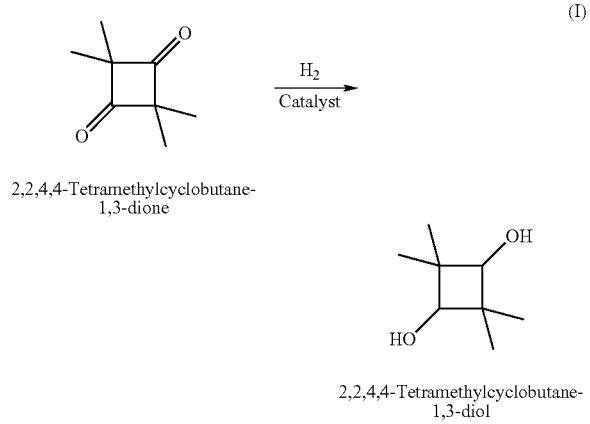

2,2,4,4-Tetramethylcyclobutane-1,3-dione 2,2,4,4-Tetramethylcyclobutane-1,3-diol (I)

1,4-Cyclohexanedimethanol is an important intermediate for producing a variety of polyester and poly(ester-amides) for coatings, fibers, molding plastics, packaging materials, and the like. 1,4-Cyclohexanedimethanol is typically manufactured by the hydrogenation of dimethylcyclohexane-1,4-dicarboxylate as shown below.

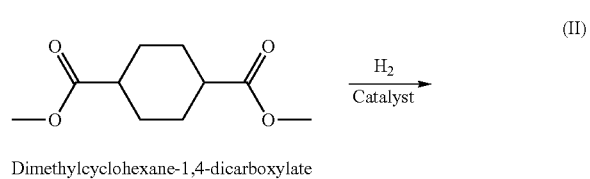

Dimethylcyclohexane-1,4-dicarboxylate (II)

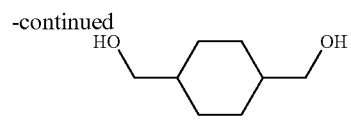

1,4-Cyclohexanedimethanol

Both 1,4-cyclohexanedimethanol and 2,2,4,4-tetramethylcyclobutane-1,3-diol are important intermediates for polyesters. For example, polyesters derived from 1,4-cyclohexanedimethanol and 2,2,4,4-tetramethylcyclobutane-1,3-diol can possess higher glass transition temperatures, superior weatherability, and/or hydrolytic stability compared to like polyesters prepared from other commonly-used, polyester-forming diols. It would be desirable to co-produce 1,4-cyclohexanedimethanol and 2,2,4,4-tetramethylcyclobutane-1,3-diol in one hydrogenation process. The present disclosure is directed to such processes.

SUMMARY OF THE INVENTION

The present disclosure pertains to processes for the simultaneous co-production of 2,2,4,4-tetramethylcyclobutane-1,3-diol and 1,4-cyclohexanedimethanol by hydrogenation 2,2,4,4-tetramethylcyclobutane-1,3-dione and dimethylcyclohexane-1,4-dicarboxylate, respectively, under hydrogenation conditions of temperature and pressure sufficient to form a 2,2,4,4-tetraalkylcyclobutane-1,3-diol and 1,4-cyclohexanedimethanol.

Additional objects and advantages of the invention will be set forth in part in the description which follows, and in part will be obvious from the description, or may be learned by practice of the invention. At least one of the objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present disclosure may be understood more readily by reference to the following detailed description of certain embodiments of the invention and the working examples.

In accordance with the purpose of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example, 1, 2, 3, 4, etc., as well as the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an," and "the" include their plural referents unless the context clearly dictates otherwise. For example, reference to the processing or making of a "catalyst," or a "promoter," is intended to include the processing or making of a plurality of catalysts, or promoters. References to a composition containing or including "a" promoter or "a" catalyst is intended to include other promoters or other catalysts, respectively, in addition to the one named.

By "comprising" or "containing" or "including" we mean that at least the named compound, element, particle, or method step, etc., is present in the composition or article or method, but we do not exclude the presence of other compounds, catalysts, materials, particles, method steps, etc., even if the other such compounds, materials, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and it is to be understood that the recited lettering can be arranged in any sequence, unless otherwise indicated.

In one embodiment, the present invention provides processes for the simultaneous co-production of 2,2,4,4-tetramethylcyclobutane-1,3-diol and 1,4-cyclohexanedimethanol. In a general embodiment, the invention provides processes for the simultaneous co-production of 2,2,4,4-tetramethylcyclobutane-1,3-diol and 1,4-cyclohexanedimethanol by hydrogenation of 2,2,4,4-tetramethylcyclobutane-1,3-dione and dimethylcyclohexane-1,4-dicarboxylate, respectively, under hydrogenation conditions of temperature and pressure sufficient to form a 2,2,4,4-tetraalkylcyclobutane-1,3-diol and 1,4-cyclohexanedimethanol. In a further embodiment, the present invention provides processes for producing 2,2,4,4-tetramethylcyclobutane-1,3-diol by use of existing 1,4-cyclohexanedimethanol production methods or by co-producing it with 1,4-cyclohexanedimethanol.

As used throughout this specification, "co-production" refers to the simultaneous production of two different desired products from essentially the same physical reactor setup. It will be readily appreciated by those skilled in the art that separate finishing steps and minor adjustments may be made at different points throughout a process to attain the different products desired. Such a process would still be within the scope and meaning of the term "co-production."

In one embodiment, the present invention provides processes for the simultaneous co-production of 2,2,4,4-tetramethylcyclobutane-1,3-diol and 1,4-cyclohexanedimethanol by hydrogenation of 2,2,4,4-tetramethylcyclobutane-1,3-dione and dimethylcyclohexane-1,4-dicarboxylate, respectively, under hydrogenation conditions of temperature and pressure sufficient to form a 2,2,4,4-tetraalkylcyclobutane-1,3-diol and 1,4-cyclohexanedimethanol. The hydrogenation reactions of the 2,2,4,4-tetraalkylcyclobutane-1,3-dione and dimethylcyclohexane-1,4-dicarboxylate can be represented by the following equation:

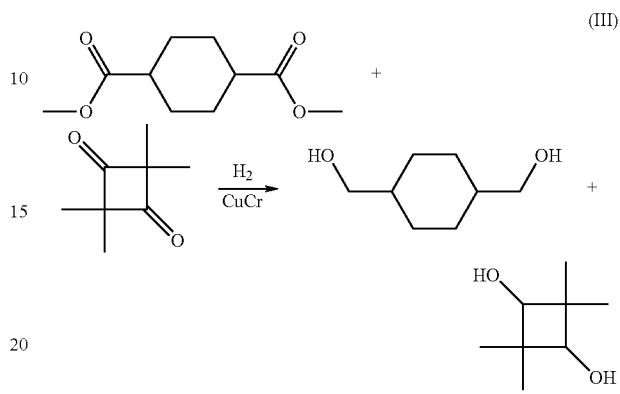

(III)

The catalyst used for hydrogenation of the 2,2,4,4-tetramethylcyclobutane-1,3-dione and dimethylcyclohexane-1,4-dicarboxylate is a copper-based catalyst. The term "copper-based catalyst" refers to a catalyst comprising copper including, for example and without limitation, zero valent copper, copper in an ionic form, and copper in an alloy.

In one embodiment, copper-based catalysts of this invention include, but are not limited to, reduced copper oxide/zinc oxide hydrogenation catalysts, reduced manganese-promoted copper catalysts, reduced copper chromite catalysts, and reduced promoted copper chromite catalysts. A "reduced catalyst" refers to a catalyst made, at least in part, by contacting a catalyst precursor compound with hydrogen to reduce at least part of the catalyst precursor to a lower valence state. In one embodiment, the copper-based catalysts of this invention include promoted copper-based catalysts. The term promoted copper-based catalyst refers to a copper-based catalyst having a promoter compound as described herein. The catalyst can be promoted by contacting the catalyst with a solution of promoter compound under appropriate conditions such that the activity of the promoted catalyst is different from the activity of the non-promoted catalyst. Applicants make no representation regarding the nature of the interaction of the promoter compound and the catalyst, but instead contemplate as within the scope of the present invention all promoted copper-based catalysts that are active in the claimed processes. In one embodiment, the catalyst may contain, as a promoter, oxides of barium or manganese to enhance the catalyst activity and/or to prevent the sintering of the catalyst.

Suitable supports for the copper-based catalysts include, but are not limited to, silica, alumina, aluminosilicate, silica/alumina, kieselguhr, titania, graphite, silicon carbide, zirconia, chromate, barium chromate, zinc oxide, clay, and alumina-clay, chromia, carbon, or a mixture of two or more thereof, for example, a mixture of chromia and carbon. Suitable forms of the support include powder, extrudate, spheres, or pellets. The shape of copper-based catalysts is not specifically limited, but catalysts of cylindrical shape which are commercially readily available are usually recommended. Further embodiments of suitable catalysts include those molded after addition of various binders in order to impart an improved strength to the catalyst.

For certain embodiments of the present invention, the processes are conducted at temperatures in the range of 150° C.

to 250° C. For certain embodiments of the present invention, the processes are conducted at pressures in the range of 13,789 kPa (2000 psi) (138 barg) to 41,368 kPa (6000 psi) (413 barg). For certain embodiments of the present invention, the processes are conducted at temperatures in the range of 160° C. to 240° C. and at pressures in the range of 17,236 kPa (2500 psi) (172 barg) to 37,921 kPa (5500 psi) (379 barg). For certain embodiments of the present invention, the processes are conducted at temperatures in the range of 170° C. to 230° C. and at pressures in the range of 20,684 kPa (3000 psi) (206 barg) to 34,473 kPa (5000 psi) (344 bar).

For certain embodiments of the present invention, the process has a temperature ranging from 150° C. to 250° C., 160° C. to 250° C., 170° C. to 250° C., 180° C. to 250° C., 190° C. to 250° C., 200° C. to 250° C., 210° C. to 250° C., 220° C. to 250° C., 230° C. to 250° C., or 240° C. to 250° C. For certain embodiments of the present invention, the process has a temperature ranging from 150° C. to 240° C., 160° C. to 240° C., 170° C. to 240° C., 180° C. to 240° C., 190° C. to 240° C., 200° C. to 240° C., 210° C. to 240° C., 220° C. to 240° C., or 230° C. to 240° C. For certain embodiments of the present invention, the process has a temperature ranging from 150° C. to 230° C., 160° C. to 230° C., 170° C. to 230° C., 180° C. to 230° C., 190° C. to 230° C., 200° C. to 230° C., 210° C. to 230° C., or 220° C. to 230° C. For certain embodiments of the present invention, the process has a temperature ranging from 150° C. to 220° C., 160° C. to 220° C., 170° C. to 220° C., 180° C. to 220° C., 190° C. to 220° C., 200° C. to 220° C., or 210° C. to 220° C. For certain embodiments of the present invention, the process has a temperature ranging from 150° C. to 210° C., 160° C. to 210° C., 170° C. to 210° C., 180° C. to 210° C., 190° C. to 210° C., or 200° C. to 210° C. For certain embodiments of the present invention, the process has a temperature ranging from 150° C. to 200° C., 160° C. to 200° C., 170° C. to 200° C., 180° C. to 200° C., or 190° C. to 200° C. For certain embodiments of the present invention, the process has a temperature ranging from 150° C. to 190° C., 160° C. to 190° C., 170° C. to 190° C., or 180° C. to 190° C. For certain embodiments of the present invention, the process has a temperature ranging from 150° C. to 180° C., 160° C. to 180° C., or 170° C. to 180° C. For certain embodiments of the present invention, the process has a temperature ranging from 150° C. to 170° C. or 160° C. to 170° C. For certain embodiments of the present invention, the process has a temperature ranging from 150° C. to 160° C.

For certain embodiments of the present invention, the process has a pressure ranging from 2000 psi to 6000 psi, 2500 psi to 6000 psi, 3000 psi to 6000 psi, 3500 psi to 6000 psi, 4000 psi to 6000 psi, 4500 psi to 6000 psi, 5000 psi to 6000 psi, or 5500 psi to 6000 psi. For certain embodiments of the present invention, the process has a pressure ranging from 2000 psi to 5500 psi, 2500 psi to 5500 psi, 3000 psi to 5500 psi, 3500 psi to 5500 psi, 4000 psi to 5500 psi, 4500 psi to 5500 psi, or 5000 psi to 5500 psi. For certain embodiments of the present invention, the process has a pressure ranging from 2000 psi to 5000 psi, 2500 psi to 5000 psi, 3000 psi to 5000 psi, 3500 psi to 5000 psi, 4000 psi to 5000 psi, or 4500 psi to 5000 psi. For certain embodiments of the present invention, the process has a pressure ranging from 2000 psi to 4500 psi, 2500 psi to 4500 psi, 3000 psi to 4500 psi, 3500 psi to 4500 psi, or 4000 psi to 4500 psi. For certain embodiments of the present invention, the process has a pressure ranging from 2000 psi to 4000 psi, 2500 psi to 4000 psi, 3000 psi to 4000 psi, or 3500 psi to 4000 psi. For certain embodiments of the present invention, the process has a pressure ranging from 2000 psi to 3500 psi, 2500 psi to 3500 psi, or 3000 psi to 3500 psi. For certain embodiments of the present invention, the process has a pressure ranging from 2000 psi to 3000 psi, or 2500 psi to 3000 psi. For certain embodiments of the present invention, the process has a pressure ranging from 2000 psi to 2500 psi.

It is contemplated that the processes of the invention can be carried out at least one of the temperature ranges disclosed herein and at least one of the pressure ranges disclosed herein.

The source and purity of the hydrogen gas used in the processes of the present invention are not critical. The hydrogen gas used in the processes may comprise fresh hydrogen or a mixture of fresh hydrogen and recycled hydrogen. The hydrogen gas can be a mixture of hydrogen and, optionally, minor amounts, typically less than 30 mole %, of components such as CO and $CO_2$, and inert gases, such as argon, nitrogen, or methane. In one embodiment, the hydrogen gas may comprise at least 70 mole % of hydrogen. For example, the hydrogen gas comprises at least 90 mole % or, in another example, at least 97 mole %, of hydrogen. The hydrogen gas may be obtained from any of the conventional sources well known in the art such as, for example, by partial oxidation or steam reforming of natural gas. Pressure swing absorption can be used if a high purity hydrogen gas is desired. If hydrogen gas recycle is utilized in one of the processes, then the recycled hydrogen gas will normally contain minor amounts of one or more products of the hydrogenation reaction that have not been fully condensed in the product recovery stage downstream from the hydrogenation zone.

The processes of this invention may be carried out in the absence of a solvent. In one embodiment of the present invention, the 2,2,4,4-tetramethylcyclobutane-1,3-dione is dissolved in the dimethylcyclohexane-1,4-dicarboxylate at a concentration of 1 to 60% (w/w), for example 5 to 50%, or 10 to 25%.

Certain embodiments of the present invention include processes comprising (1) feeding isobutyric anhydride to a pyrolysis zone to produce a vapor effluent comprising dimethylketene, isobutyric acid, and unreacted isobutyric anhydride; (2) cooling the vapor effluent to condense isobutyric acid and isobutyric anhydride and separating the condensate from the dimethylketene vapor; (3) feeding the dimethylketene vapor to an absorption zone wherein the dimethylketene vapor is dissolved in dimethylcyclohexane-1,4-dicarboxylate to produce an absorption zone effluent comprising a solution of dimethylketene in the dimethylcyclohexane-1,4-dicarboxylate; (4) feeding the absorption zone effluent to a dimerization zone wherein the absorption zone effluent is heated to convert dimethylketene to 2,2,4,4-tetramethylcyclobutanedione to produce a dimerization zone effluent comprising a solution of 2,2,4,4-tetramethylcyclobutanedione in the dimethylcyclohexane-1,4-dicarboxylate; and (5) contacting the 2,2,4,4-tetramethylcyclobutanedione and dimethylcyclohexane-1,4-dicarboxylate with hydrogen in the presence of a copper-based catalyst under conditions of temperature and pressure sufficient to form a 2,2,4,4-tetramethylcyclobutane-1,3-diol and 1,4-cyclohexanedimethanol.

Other embodiments of the present invention include processes comprising (1) feeding an isobutyric acid to a pyrolysis zone wherein the isobutyric acid produces a vapor effluent comprising dimethylketene, water, and unreacted isobutyric acid; (2) cooling the vapor effluent to condense water and isobutyric acid and separating the condensate from the dimethylketene vapor; (3) feeding the dimethylketene vapor to an absorption zone wherein the dimethylketene vapor is dissolved in dimethylcyclohexane-1,4-dicarboxylate to produce an absorption zone effluent comprising a solution of dimethylketene in the dimethylcyclohexane-1,4-dicarboxylate; (4) feeding the absorption zone effluent to a dimerization zone wherein the absorption zone effluent is heated to convert dimethylketene to 2,2,4,4-tetramethylcyclobutane-1,3-dione to produce a dimerization zone effluent comprising a solution of 2,2,4,4-tetramethylcyclobutane-1,3-dione in the dimethyl-cyclohexane-1,4-dicarboxylate; and (5) contacting the 2,2,4,4-tetramethylcyclobutane-1,3-dione and dimethylcyclohexane-1,4-dicarboxylate with hydrogen in the presence of a copper-based catalyst under conditions of temperature and pressure sufficient to form a 2,2,4,4-tetramethylcyclobutane-1,3-diol and 1,4-cyclohexanedimethanol.

The nature of the process for making the dimethylketene is not critical and any conventional method may be used including, but not limited to, the methods disclosed in U.S. Pat. Nos. 1,602,699; 2,160,841; 2,202,046; 2,278,537; 2,806,064; 3,201,474; 3,259,469; 3,366,689; 3,403,181; 5,475,144; and 6,232,504. These documents are hereby incorporated by reference for their disclosure of methods for making a suitable dimethylketene. Processes for the preparation of dimethylketene and 2,2,4,4-tetramethylcyclobutane-1,3-dione may be combined with all aspects of the present invention.

All of these novel processes may be carried out as a batch, semi-continuous, or continuous process and may utilize a variety of reactor types. Examples of suitable reactor types include, but are not limited to, stirred tank, continuous stirred tank, slurry, tubular, fixed bed, and trickle bed. The term "continuous" as used herein means a process wherein reactants are introduced and products withdrawn simultaneously in an uninterrupted manner. By "continuous" it is meant that the process is substantially or completely continuous in operation, in contrast to a "batch" process. "Continuous" is not meant in any way to exclude normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed into or removed from the reactor. For example, in a batch operation, a slurry of the catalyst in the cyclobutanedione and/or a solvent in which the cyclobutanedione has been dissolved is fed to a pressure vessel equipped with means for agitation. The pressure vessel is then pressurized with hydrogen to a predetermined pressure followed by heating to bring the reaction mixture to the desired temperature. After the hydrogenation is complete, the reaction mixture is removed from the pressure vessel, the catalyst is separated by filtration, and the 2,2,4,4-tetramethylcyclobutane-1,3-diol product is isolated, for example, in a distillation train or by crystallization. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

In one embodiment the process may be operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular, or columnar reactor and the liquid 2,2,4,4-tetramethylcyclobutane-1,3-dione and dimethylcyclohexane-1,4-dicarboxylate, fed continuously into the top of the bed at elevated pressure and temperature, and the crude hydrogenation product removed from the base of the reactor. Alternatively, it is possible to feed the 2,2,4,4-tetramethylcyclobutane-1,3-dione and dimethylcyclohexane-1,4-dicarboxylate into the bottom of the bed and remove the crude product from the top of the reactor. It is also possible to use two or more catalyst beds or hydrogenation zones connected in parallel or in series to improve conversion, to reduce the quantity of catalyst, or to by-pass a catalyst bed for periodic maintenance or catalyst removal. Another mode of continuous operation utilizes a slurry of the catalyst in an agitated pressure vessel which is equipped with a filter leg to permit continuous removal of a solution of product in unreacted 2,2,4,4-tetramethylcyclobutane-1,3-dione and dimethylcyclohexane-1,4-dicarboxylate. In this manner a liquid reactant or reactant solution can be continuously fed to, and product solution continuously removed from, an agitated pressure vessel containing an agitated slurry of the catalyst.

In one embodiment, the present invention provides processes for the co-production of 2,2,4,4-tetramethylcyclobutane-1,3-diol and 1,4-cyclohexanedimethanol comprising contacting a mixture comprising 2,2,4,4-tetramethylcyclobutane-1,3-dione and dimethylcyclohexane-1,4-dicarboxylate with a copper-based catalyst in the presence of hydrogen under conditions of pressure and temperature sufficient to convert at least a portion of the 2,2,4,4-tetramethylcyclobutane-1,3-dione and at least a portion of the dimethylcyclohexane-1,4-dicarboxylate to 2,2,4,4-tetramethylcyclobutane-1,3-diol and 1,4-cyclohexanedimethanol, respectively, to form a crude product stream.

In one embodiment of the present invention, the dimethylcyclohexanedicarboxylate is selected from the group consisting of dimethylcyclohexane-1,2-dicarboxylate, dimethylcyclohexane-1,3-dicarboxylate, dimethylcyclohexane-1,4-dicarboxylate and mixtures thereof.

In one embodiment of the present invention, the dimethylcyclohexanedicarboxylate is dimethylcyclohexane-1,4-dicarboxylate.

In one embodiment of the present invention, the catalyst comprises a copper-based catalyst. In one embodiment of the present invention, the catalyst comprises a copper chromite catalyst.

In one embodiment of the present invention, the hydrogenation process has a temperature ranging from 150° C. to 250° C. In one embodiment of the present invention, the hydrogenation process has a temperature ranging from 185° C. to 225° C. In one embodiment of the present invention, the hydrogenation process has a pressure ranging from 13,789 kPa (2000 psi) to 41,3768 kPa (6000 psi).

In one embodiment of the present invention, the mixture of 2,2,4,4-tetramethylcyclobutane-1,3-dione and dimethylcyclohexane-1,4-dicarboxylate comprises from 1 wt % to 60 wt % 2,2,4,4-tetramethylcyclobutane-1,3-dione, based on the total weight of the 2,2,4,4-tetramethylcyclobutane-1,3-dione and dimethylcyclohexane-1,4-dicarboxylate. In one embodiment of the present invention, the mixture of 2,2,4,4-tetramethylcyclobutane-1,3-dione and dimethylcyclohexane-1,4-dicarboxylate comprises from 5 wt % to 50 wt % 2,2,4,4-tetramethylcyclobutane-1,3-dione, based on the total weight of the 2,2,4,4-tetramethylcyclobutane-1,3-dione and dimethylcyclohexane-1,4-dicarboxylate. In one embodiment of the present invention, the mixture of 2,2,4,4-tetramethylcyclobutane-1,3-dione and dimethylcyclohexane-1,4-dicarboxylate comprises from 10 wt % to 25 wt % 2,2,4,4-tetramethylcyclobutane-1,3-dione, based on the total weight of the 2,2,4,4-tetramethylcyclobutane-1,3-dione and dimethylcyclohexane-1,4-dicarboxylate.

In one embodiment of the present invention, the dimethylcyclohexanedicarboxylate is chosen from dimethylcyclohexane-1,2-dicarboxylate, dimethylcyclohexane-1,3-dicarboxylate, dimethylcyclohexane-1,4-dicarboxylate and mixtures thereof. In one embodiment of the present invention, the cyclohexanedicarboxylate is dimethylcyclohexane-1,4-dicarboxylate.

In one embodiment, the present invention provides processes for the co-production of 2,2,4,4-tetramethylcyclobutane-1,3-diol and dimethylcyclohexanedimethanol comprising contacting a mixture comprising 2,2,4,4-tetramethylcyclobutane-1,3-dione and dimethylcyclohexane-1,4-dicarboxylate with a copper-based catalyst in the presence of hydrogen under conditions of pressure and temperature sufficient to convert at least a portion of the 2,2,4,4-tetramethylcyclobutane-1,3-dione and at least a portion of the dimethylcyclohexane-1,4-dicarboxylate to 2,2,4,4-tetramethylcyclobutane-1,3-diol and 1,4-cyclohexanedimethanol, respectively, to form a crude product stream, wherein at least a portion of the 2,2,4,4-tetramethylcyclobutane-1,3-diol and 1,4-cyclohexanedimethanol is separated from the crude product to form a depleted product stream. In one embodiment of the present invention, the depleted product stream is recycled with a mixture comprising 2,2,4,4-tetramethylcyclobutane-1,3-dione and dimethylcyclohexane-1,4-dicarboxylate. The term "depleted product stream" means a stream having less 2,2,4,4-tetramethylcyclobutane-1,3-diol and/or less 1,4-cyclohexanedimethanol than the product stream from which it is obtained.

In one embodiment, the present invention provides processes comprising (1) feeding isobutyric anhydride to a pyrolysis zone produce a vapor effluent comprising dimethylketene, isobutyric acid and unreacted isobutyric anhydride; (2) cooling the vapor effluent to condense isobutyric acid and isobutyric anhydride and separating the condensate from the dimethylketene vapor; (3) feeding the dimethylketene vapor to an absorption zone wherein the dimethylketene vapor is dissolved dimethylcyclohexane-1,4-dicarboxylate to produce an absorption zone effluent comprising a solution of dimethylketene in the dimethylcyclohexane-1,4-dicarboxylate; (4) feeding the absorption zone effluent to a dimerization zone wherein the absorption zone effluent is heated to convert dimethylketene to 2,2,4,4-tetramethylcyclobutane-1,3-dione to produce a dimerization zone effluent comprising a solution of 2,2,4,4-tetramethylcyclobutane-1,3-dione in the dimethylcyclohexane-1,4-dicarboxylate; and (5) contacting the 2,2,4,4-tetramethylcyclobutane-1,3-dione and dimethylcyclohexane-1,4-dicarboxylate with hydrogen in the presence of a copper-based catalyst under conditions of temperature and pressure sufficient to form a 2,2,4,4-tetramethylcyclobutane-1,3-diol and cyclohexanedimethanol. In one embodiment of the present invention, the dimethylcyclohexane-1,4-dicarboxylate is selected from the group consisting of 1,2-dimethylcyclohexane-1,4-dicarboxylate, 1,3-dimethylcyclohexane-1,4-dicarboxylate and 1,4-dimethylcyclohexane-1,4-dicarboxylate. In one embodiment of the present invention, the dimethylcyclohexanedicarboxylate comprises 1,4-dimethylcyclohexane-1,4-dicarboxylate.

In one embodiment, the present invention also provides processes for the simultaneous co-production of 2,2,4,4-tetramethylcyclobutane-1,3-diol and 1,4-cyclohexanedimethanol by continuously feeding 2,2,4,4-tetramethylcyclobutane-1,3-dione, dimethylcyclohexane-1,4-dicarboxylate, and hydrogen to a hydrogenation zone comprising a copper-based catalyst at pressure of 13,789 kPa (2000 psi) (138 barg) to 41,368 kPa (6000 psi) (413 barg) and a hydrogenation temperature of 175° C. to 250° C. and continuously recovering from said hydrogenation zone an effluent comprising 2,2,4,4-tetramethylcyclobutane-1,3-diol and 1,4-cyclohexanedimethanol. In another embodiment, the process may further comprise continuously recycling a portion of the effluent to the hydrogenation zone. The hydrogenation zone may be any suitable reactor type including, but are not limited to, a stirred tank, a continuous stirred tank, a slurry reactor, a tubular reactor, a fixed bed, and a trickle bed. For example, the processes of the invention may be carried out in a trickle bed reactor operated in the liquid phase. Certain embodiments of the invention are further described and illustrated by the following examples.

In one embodiment, the present invention also provides processes for the co-production of 2,2,4,4-tetramethylcyclobutane-1,3-diol and a second diol comprising contacting a mixture comprising 2,2,4,4-tetramethylcyclobutane-1,3-dione and reactive solvent with a copper-based catalyst in the presence of hydrogen under conditions of pressure and temperature sufficient to convert at least a portion of the 2,2,4,4-tetramethylcyclobutane-1,3-dione into 2,2,4,4-tetramethylcyclobutane-1,3-diol and at least a portion of the reactive solvent into the second diol. The term "reactive solvent" means a compound used as a solvent for the 2,2,4,4-tetramethylcyclobutane-1,3-dione and/or the 2,2,4,4-tetramethylcyclobutane-1,3-diol, wherein the reactive solvent is reduced under the hydrogenation conditions for the reduction of 2,2,4,4-tetramethylcyclobutane-1,3-dione. The catalyst may comprise any of the copper-based catalysts described above including, but not limited to, copper chromite or copper-based catalysts promoted with barium, magnesium, or mixtures thereof. The range of temperatures and pressures for previously described embodiments according to the present invention are applicable to this embodiment.

In one embodiment, the reactive solvent is a diester including, but not limited to, a dimethylcyclohexanedicarboxylate such as the 1,2-, 1,3- and/or 1,4-dimethylcyclohexanedicarboxylate and would form the corresponding cyclohexanedimethanol. Dimethylcyclohexane-1,4-dicarboxylate was an unexpectedly good solvent for the 2,2,4,4-tetramethylcyclobutane-1,3-dione. Since the dimethylcyclohexane-1,4-dicarboxylate has a relatively low melting point of 25° C. and the 2,2,4,4-tetramethylcyclobutane-1,3-dione has a melting point of 140° C., it was uncertain that the dimethylcyclohexane-1,4-dicarboxylate would function adequately as a solvent for the 2,2,4,4-tetramethylcyclobutane-1,3-dione.

In one embodiment, the 2,2,4,4-tetramethylcyclobutane-1,3-diol and the second diol, for example, 1,4-cyclohexanedimethanol, may be used in copolyester production without separating the 2,2,4,4-tetramethylcyclobutane-1,3-diol and the second diol.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Further embodiments of the invention include:

A process for the co-production of 2,2,4,4-tetramethylcyclobutane-1,3-diol and cyclohexanedimethanol comprising contacting a mixture comprising 2,2,4,4-tetramethylcyclobutane-1,3-dione and dimethylcyclohexane-1,4-dicarboxylate with a copper-based catalyst in the presence of hydrogen under conditions of pressure and temperature sufficient to convert at least a portion of the 2,2,4,4-tetramethylcyclobutane-1,3-dione into 2,2,4,4-tetramethylcyclobutane-1,3-diol and at least a portion of the dimethylcyclohexane-1,4-dicarboxylate into cyclohexanedimethanol.

The process according to paragraph 47, wherein the cyclohexanedicarboxylate is chosen from 1,2-cyclohexanedicarboxylate, 1,3-cyclohexanedicarboxylate, 1,4-cyclohexanedicarboxylate, and mixtures thereof.

The process according to any of the embodiments in paragraphs 47-48, wherein the copper-based catalyst comprises a promoted copper-based catalyst.

The process according to any of the embodiments in paragraphs 47-49, wherein the promoted copper-based catalyst comprises barium or manganese.

The process according to any of the embodiments in paragraphs 47-50, wherein the catalyst comprises a copper chromite catalyst.

The process according to any of the embodiments in paragraphs 47-51, wherein the temperature of the process is from 150° C. to 250° C.

The process according to any of the embodiments in paragraphs 47-52, wherein the temperature of the process is from 185° C. to 225° C.

The process according to any of the embodiments in paragraphs 47-53, wherein the pressure of the process is from 2000 psi to 6000 psi.

The process according to any of the embodiments in paragraphs 47-54, wherein the pressure of the process is from 2500 psi to 5500 psi.

The process according to any of the embodiments in paragraphs 47-55, wherein the cyclohexanedicarboxylate is 1,4-cyclohexanedicarboxylate.

The process according to any of the embodiments in paragraphs 47-56, wherein the mixture of 2,2,4,4-tetramethylcyclobutane-1,3-dione and dimethylcyclohexane-1,4-dicarboxylate comprises from 1 wt % to 60 wt % dimethylcyclohexane-1,4-dicarboxylate, based on the total weight of the 2,2,4,4-tetramethylcyclobutane-1,3-dione and dimethylcyclohexane-1,4-dicarboxylate.

The process according to any of the embodiments in paragraphs 47-57, wherein the mixture of 2,2,4,4-tetramethylcyclobutane-1,3-dione and dimethylcyclohexane-1,4-dicarboxylate comprises from 5 wt % to 50 wt % dimethylcyclohexane-1,4-dicarboxylate, based on the total weight of the 2,2,4,4-tetramethylcyclobutane-1,3-dione and dimethylcyclohexane-1,4-dicarboxylate.

The process according to any of the embodiments in paragraphs 47-58, wherein the mixture of 2,2,4,4-tetramethylcyclobutane-1,3-dione and dimethylcyclohexane-1,4-dicarboxylate comprises from 10 wt % to 25 wt % dimethylcyclohexane-1,4-dicarboxylate, based on the total weight of the 2,2,4,4-tetramethylcyclobutane-1,3-dione and dimethylcyclohexane-1,4-dicarboxylate.

The process according to any of the embodiments in paragraphs 47-59, wherein the cyclohexanedicarboxylate is chosen from 1,2-cyclohexanedicarboxylate, 1,3-cyclohexanedicarboxylate, 1,4-cyclohexanedicarboxylate, and mixtures thereof.

The process according to any of the embodiments in paragraphs 47-60, wherein the cyclohexanedicarboxylate is 1,4-cyclohexanedicarboxylate.

The process according to any of the embodiments in paragraphs 47-61, wherein at least a portion of the 2,2,4,4-tetramethylcyclobutane-1,3-diol and at least a portion of the cyclohexanedimethanol are separated from the crude product to form a depleted product stream.

The process according to any of the embodiments in paragraphs 47-62, wherein the depleted product stream is recycled to the mixture comprising 2,2,4,4-tetramethylcyclobutane-1,3-dione and dimethylcyclohexane-1,4-dicarboxylate.

A process comprising
(1) feeding isobutyric anhydride to a pyrolysis zone to produce a vapor effluent comprising dimethylketene, isobutyric acid and unreacted isobutyric anhydride;
(2) cooling the vapor effluent to condense isobutyric acid and isobutyric anhydride and separating the condensate from the dimethylketene vapor;
(3) feeding the dimethylketene vapor to an absorption zone wherein the dimethylketene vapor is dissolved in a dimethylcyclohexane-1,4-dicarboxylate to produce an absorption zone effluent comprising a solution of dimethylketene in the dimethylcyclohexane-1,4-dicarboxylate;
(4) feeding the absorption zone effluent to a dimerization zone wherein the absorption zone effluent is heated to convert dimethylketene to 2,2,4,4-tetramethylcyclobutane-1,3-dione to produce a dimerization zone effluent comprising a solution of 2,2,4,4-tetramethylcyclobutane-1,3-dione in the dimethylcyclohexane-1,4-dicarboxylate; and
(5) contacting the 2,2,4,4-tetramethylcyclobutane-1,3-dione and dimethylcyclohexane-1,4-dicarboxylate with hydrogen in the presence of a copper-based catalyst under conditions of temperature and pressure sufficient to form a 2,2,4,4-tetramethylcyclobutane-1,3-diol and cyclohexanedimethanol.

The process according to the embodiment in paragraph 64, wherein the dimethylcyclohexane-1,4-dicarboxylate is chosen from 1,2-dimethylcyclohexane-1,4-dicarboxylate, 1,3-dimethylcyclohexane-1,4-dicarboxylate, 1,4-dimethylcyclohexane-1,4-dicarboxylate, and mixtures thereof.

The process according to any of the embodiments in paragraphs 64-65, wherein the dimethylcyclohexane-1,4-dicarboxylate comprises 1,4-dimethylcyclohexane-1,4-dicarboxylate.

The process according to any of the embodiments in paragraphs 64-66, wherein the catalyst comprises a copper chromite catalyst.

A process comprising
(1) feeding an isobutyric acid to a pyrolysis zone wherein the isobutyric acid produces a vapor effluent comprising dimethylketene, water, and unreacted isobutyric acid;
(2) cooling the vapor effluent to condense water and isobutyric acid and separating the condensate from the dimethylketene vapor;
(3) feeding the dimethylketene vapor to an absorption zone wherein the dimethylketene vapor is dissolved in dimethylcyclohexane-1,4-dicarboxylate to produce an absorption zone effluent comprising a solution of dimethylketene in the dimethylcyclohexane-1,4-dicarboxylate;
(4) feeding the absorption zone effluent to a dimerization zone wherein the absorption zone effluent is heated to convert dimethylketene to 2,2,4,4-tetramethylcyclobutane-1,3-dione to produce a dimerization zone effluent comprising a solution of 2,2,4,4-tetramethylcyclobutane-1,3-dione in the dimethylcyclohexane-1,4-dicarboxylate; and
(5) contacting the 2,2,4,4-tetramethylcyclobutane-1,3-dione and dimethylcyclohexane-1,4-dicarboxylate with hydrogen in the presence of a copper-based catalyst under conditions of temperature and pressure sufficient to form a 2,2,4,4-tetramethylcyclobutane-1,3-diol and 1,4-cyclohexanedimethanol.

The process according to the embodiment in paragraph 68, wherein the dimethylcyclohexane-1,4-dicarboxylate is chosen from 1,2-dimethylcyclohexane-1,4-dicarboxylate, 1,3-dimethylcyclohexane-1,4-dicarboxylate, 1,4-dimethylcyclohexane-1,4-dicarboxylate, and mixtures thereof.

The process according to any of the embodiments in paragraphs 68-69, wherein the dimethylcyclohexane-1,4-dicarboxylate comprises 1,4-dimethylcyclohexane-1,4-dicarboxylate.

The process according to any of the embodiments in paragraphs 68-70, wherein the catalyst comprises a copper chromite catalyst.

EXAMPLES

The following examples illustrate in general the processes of the present invention for the simultaneous co-production of 2,2,4,4-tetramethylcyclobutane-1,3-diol and 1,4-cyclohexanedimethanol by hydrogenation of 2,2,4,4-tetramethylcyclobutane-1,3-dione and dimethylcyclohexane-1,4-dicarboxylate.

General

The following is a general description of the reactor system, hydrogenation process, and analytical methods used henceforward in the Examples described below unless otherwise specified.

The experiments were carried out in a continuous mode of operation in a vertical trickle bed reactor having a length of 72 inches (1.83 m) and an inside diameter of 1 inch (25.4 mm). The reactor temperature was monitored by a series of ten thermocouples inserted into the wall of the reactor. The reactor was loaded with sufficient solid catalyst to fill a volume of 500 ml and then filled to capacity with glass beads (approximately enough to fill a volume of 396 ml). The catalyst was an E-406 copper chromite catalyst obtained from BASF. The reactor was then rinsed with several gallons of methanol to remove any fine particulates. The catalyst was reduced with hydrogen in-situ prior to testing. The catalyst reduction was carried out in the presence of 1,4-cyclohexanedimethanol at 345 barg (34,500 kPa). Temperature was increased from ambient temperature to 200° C. over a period of 4.5 hours.

A 15 wt % solution of 2,2,4,4-tetramethylcyclobutane-1,3-dione in dimethylcyclohexane-1,4-dicarboxylate was used as the starting feed. The feed reservoir was a jacked 4 L graduated vessel with a bottom take-off valve. Molten feed was pumped through a high-pressure syringe pump into a recycle stream and then through a pre-heater to raise the feed temperature to the approximate reactor temperature. The reservoir, pump head, and feed lines were steam heated to prevent the feed from freezing. Three zone heaters on the reactor were used to establish an approximate isothermal temperature profile during the experiment.

The feed/recycle mixture was fed at the top of the reactor vessel along with hydrogen and contacted with the catalyst. Crude product was removed from the bottom of the reactor and fed to a level pot wherein hydrogen was separated from the crude product. A portion of the crude product was removed from the production system and the remainder recycled. The liquid hold-up in the reactor system was approximately 1 L. After the system reached the correct process settings of temperature, pressure, feed rate, and recycle rate, the system was held at these conditions for the appropriate amount of time (3 full bed turnovers). Although the recycle rates were somewhat variable, the typical recycle rate was estimated to be about 11-12 L/hr.

The product samples were analyzed by GC analysis as follows. A sample was heated to approximately 100° C. until the sample was solubilized. Ten drops of the reaction sample were diluted with 1.5 ml dimethylsulfoxide and analyzed by capillary gas-liquid chromatography ("GC") using an Agilent 6890N Gas Chromatograph equipped with a flame ionization detector (FID) and split/splitless injection system. The GC samples were injected onto a 0.5 micron (30 m×0.25 mm) DB®-Wax column. For each analysis, the initial temperature of the column was set at 50° C., held for 4 minutes, ramped to 125° C. at a rate of 12° C./min, ramped to 165° C. at a rate of 3° C./min, held for at 165° C. for 2 minutes, ramped to 240° C. at a rate of 15° C./min, and held at 240° C. for 15 minutes. Results are given as GC area percentages.

The following abbreviations apply throughout the working examples and tables:

| | |
|---|---|
| TMCB | 2,2,4,4-tetramethylcyclobutane-1,3-dione |
| Ring-open Ketol | 1-hydroxy-2,2,4-trimethyl-3-pentanone (a product of the partial hydrogenation and ring opening of 2,2,4,4-tetramethylcyclobutane-1,3-dione) |
| Cyclic Ketol | 3-hydroxy-2,2,4,4-tetramethylcyclobutanone (a product of the partial hydrogenation of 2,2,4,4-tetramethylcyclobutane-1,3-dione) |
| TMPD | 2,2,4-trimethyl-1,3-pentanediol (a product of the hydrogenation of Ring-open Ketol) |
| TMCD | 2,2,4,4-tetramethylcyclobutane-1,3-diol |
| Cis-TMCD | cis-2,2,4,4-tetramethylcyclobutane-1,3-diol |
| Trans-TMCD | trans-2,2,4,4-tetramethylcyclobutane-1,3-diol |
| DMCD | dimethylcyclohexane-1,4-dicarboxylate |
| CHDM Monoesters | cis and trans isomers of 4-(hydroxymethyl)cyclohexanecarboxylate (products of the partial hydrogenation of DMCD) |
| CHDM | 1,4-cyclohexanedimethanol |
| Cis-CHDM | cis-1,4-cyclohexanedimethanol |
| Trans-CHDM | trans-1,4-cyclohexanedimethanol |

The conversion and yield of the hydrogenation processes as well as the cis/trans ratio of the 2,2,4,4-tetramethylcyclobutane-1,3-diol and 1,4-cyclohexanedimethanol products were calculated on the basis of GC area percentages using the following formulas:

$$TMCB\ \text{Conversion}\ \% = \frac{(\text{moles}\ TMCB\ \text{fed}) - (\text{moles}\ TMCB\ \text{remaining})}{(\text{moles}\ TMCB\ \text{fed})} \times 100$$

$$DMCD\ \text{Conversion}\ \% = \frac{(\text{moles}\ DMCD\ \text{fed}) - (\text{moles}\ DMCD\ \text{remaining})}{(\text{moles}\ DMCD\ \text{fed})} \times 100$$

$$TMCD\ \text{Selectivity} = \frac{(\text{moles}\ cis - TMCD) + (\text{moles}\ trans - TMCD)}{(\text{moles}\ TMCB\ \text{fed}) - (\text{moles}\ TMCB\ \text{remaining})} \times 100$$

$$CHDM\ \text{Selectivity} = \frac{(\text{moles}\ Cis - CHDM) + (\text{moles}\ Trans - CHDM)}{(\text{moles}\ DMCD\ \text{fed}) - (\text{moles}\ DMCD\ \text{remaining})} \times 100$$

$$TMCD\ \text{Yield}\ \% = \frac{(\text{moles}\ cis - TMCD) + (\text{moles}\ Trans - TMCD)}{(\text{moles}\ TMCB\ \text{fed})} \times 100$$

$$CHDM\ \text{Yield}\ \% = \frac{(\text{moles}\ Cis - CHDM) + (\text{moles}\ Trans - CHDM)}{(\text{moles}\ DMCD\ \text{fed})} \times 100$$

$$TMCD\ Cis/Trans\ \text{Ratio} = \frac{(\text{moles}\ cis - TMCD)}{(\text{moles}\ Trans - TMCD)}$$

$$CHDM\ Cis/Trans\ \text{Ratio} = \frac{(\text{moles}\ Cis - CHDM)}{(\text{moles}\ Trans - CHDM)}$$

Comparative Example 1

Using the general procedure described above, a solution of DMCD was hydrogenated at temperatures ranging from 150° C. to 225° C. and pressures ranging from 500 to 5000 psi. The feed rate ranged from 0.6 to 1.3 L/hr. The results are shown in Table 1.

TABLE 1

Hydrogenation of DMCD to CHDM

|  | Comparative Example | | | | | | |
|---|---|---|---|---|---|---|---|
|  | 1a | 1b | 1c | 1d | 1e | 1f | 1g |
| Temperature (° C.) | 150 | 150 | 150 | 150 | 205 | 215 | 225 |
| Pressure (psi) | 500 | 1000 | 2000 | 5000 | 5000 | 5000 | 5000 |
| Feed Rate (L/hr) | 1.3 | 1.3 | 1.3 | 1.3 | 1.5 | 1.5 | 1.5 |
| DMCD % | 98.8 | 97.7 | 95.9 | 85.2 | 34.2 | 26.7 | 17.6 |
| CHDM Monoester 1% | 0.1 | 1.0 | 1.9 | 5.7 | 10.8 | 7.8 | 6.6 |
| CHDM Monoester 2% | 0.0 | 0.5 | 0.8 | 2.4 | 5.3 | 4.0 | 3.4 |
| Cis-CHDM % | 0.0 | 0.0 | 0.035 | 1.4 | 11.2 | 18.5 | 27.6 |
| Trans-CHDM % | 0.0 | 0.0 | 0.044 | 1.6 | 13.7 | 16.3 | 20.9 |
| DMCD Conversion % | 0.9 | 2.1 | 3.8 | 14.1 | 60.9 | 70.0 | 81.8 |
| CHDM Selectivity % | 0.0 | 0.0 | 0.1 | 4.1 | 39.4 | 54.4 | 69.5 |
| CHDM Yield % | 0 | 0 | 0.004 | 0.6 | 24.0 | 38.1 | 56.8 |
| CHDM Cis/Trans |  |  | 1.26 | 1.14 | 1.22 | 0.88 | 0.76 |

Example 2

Using the general procedure described above, a 15 wt % solution of TMCB in DMCD was hydrogenated at temperatures ranging from 150° C. to 225° C. and pressures ranging from 500 to 5000 psi. The feed rate ranged from 0.6 to 1.3 L/hr. The results are shown in Table 2.

TABLE 2

Simultaneous co-production of 2,2,4,4-tetramethylcyclobutane-1,3-diol and 1,4-cyclohexanedimethanol by hydrogenation of TMCB and DMCD.

|  | Example | | | | | | | |
|---|---|---|---|---|---|---|---|---|
|  | 2a | 2b | 2c | 2d | 2e | 2f | 2g | 2h |
| Temperature (° C.) | 150 | 150 | 150 | 185 | 185 | 195 | 205 | 225 |
| Pressure (psi) | 500 | 1000 | 5000 | 5000 | 5000 | 5000 | 5000 | 5000 |
| Feed Rate (L/hr) | 1.3 | 1.3 | 1.3 | 0.6 | 1.3 | 1.3 | 1.3 | 0.6 |
| TMCB % | 2.8 | 5.8 | 0.6 | 0.0 | 0.0 | 0.0 | 0.0 | 0.0 |
| Ring-Open Ketol % | 0.0 | 0.0 | 0.0 | 0.1 | 0.1 | 0.1 | 0.0 | 0.1 |
| Cyclic Ketol % | 3.0 | 1.7 | 1.1 | 0.0 | 0.1 | 0.0 | 0.0 | 0.0 |
| TMPD % | 0.1 | 0.2 | 0.4 | 6.4 | 6.2 | 6.9 | 5.7 | 2.5 |
| DMCD % | 83.4 | 83.3 | 76.3 | 9.4 | 29.7 | 19.1 | 16.1 | 6.7 |
| CHDM Monoester 1% | 0.2 | 0.2 | 3.6 | 4.5 | 9.4 | 7.4 | 6.9 | 3.8 |
| CHDM Monoester 2% | 0.1 | 0.1 | 1.5 | 2.2 | 4.6 | 3.7 | 3.4 | 2.0 |
| Cis-TMCD % | 2.8 | 2.3 | 4.5 | 1.3 | 3.7 | 2.2 | 1.5 | 0.3 |
| Trans-TMCD % | 7.0 | 5.7 | 10.7 | 1.4 | 4.7 | 2.6 | 1.6 | 0.3 |
| Cis-CHDM % | 0.04 | 0.04 | 0.2 | 25.4 | 14.3 | 21.3 | 25.4 | 42.1 |
| Trans-CHDM % | 0.02 | 0.02 | 0.4 | 33.4 | 20.1 | 26.3 | 28.3 | 27.8 |
| TMCB Conversion % | 81.9 | 62.8 | 96.4 | 100 | 99.9 | 100 | 100 | 100 |
| TMCD Selectivity % | 61.7 | 50.4 | 87.4 | 29.4 | 56.4 | 40.7 | 35.1 | 20.7 |
| TMCD Yield % | 50.5 | 31.7 | 84.3 | 29.4 | 56.3 | 40.7 | 35.1 | 20.7 |
| TMCD Cis/Trans | 0.40 | 0.41 | 0.42 | 0.90 | 0.79 | 0.85 | 0.89 | 1.04 |
| DMCD Conversion % | 1.2 | 1.5 | 8.9 | 91.5 | 69.9 | 82.1 | 85.7 | 94.6 |

TABLE 2-continued

Simultaneous co-production of 2,2,4,4-tetramethylcyclobutane-1,3-diol and 1,4-cyclohexanedimethanol by hydrogenation of TMCB and DMCD.

| | Example | | | | | | | |
|---|---|---|---|---|---|---|---|---|
| | 2a | 2b | 2c | 2d | 2e | 2f | 2g | 2h |
| CHDM Selectivity % | 0.1 | 0.1 | 1.0 | 73.9 | 48.4 | 61.7 | 66.1 | 78.7 |
| CHDM Yield % | 0.001 | 0.002 | 0.1 | 67.6 | 33.8 | 50.7 | 56.6 | 74.4 |
| CHDM Cis/Trans | 0.41 | 0.42 | 1.85 | 1.32 | 1.40 | 1.23 | 1.12 | 0.68 |

The invention claimed is:

1. A process for the co-production of 2,2,4,4-tetramethylcyclobutane -1,3-diol and cyclohexanedimethanol comprising contacting a mixture comprising 2,2,4,4-tetramethylcyclobutane-1,3-dione and dimethylcyclohexanedicarboxylate with a copper-based catalyst in the presence of hydrogen under conditions of pressure ranciinci from about 2000 to about 6000 psig and temperature ranging from about 170 to about 210°C. to yield at least about 25 wt % of the 2,2,4,4-tetramethylcyclobutane-1,3-dione into 2,2,4,4-tetramethylcyclobutane-1,3-diol and at least about 30 wt % of the dimethylcyclohexanedicarboxylate into cyclohexanedimethanol.

2. The process according to claim 1, wherein the cyclohexanedicarboxylate is chosen from dimethylcyclohexane-1,2-dicarboxylate, dimethylcyclohexane-1,3-dicarboxylate, dimethylcyclohexane-1,4-dicarboxylate, and mixtures thereof.

3. The process according to claim 1, wherein the copper-based catalyst comprises a promoted copper-based catalyst.

4. The process according to claim 3, wherein the promoted copper based catalyst comprises barium or manganese.

5. The process according to claim 1, wherein the catalyst comprises a copper chromite catalyst.

6. The process according to claim 1, wherein the temperature of the process is from 185° C to 210° C.

7. The process according to claim 1, wherein the pressure of the process is from 2500 psi to 5500 psi.

8. The process according to claim 2, wherein the dimethylcyclohexanedicarboxylate is 1,4-cyclohexanedicarboxylate.

9. The process according to claim 1, wherein the mixture of 2,2,4,4-tetramethylcyclobutane-1,3-dione and dimethylcyclohexanedicarboxylate comprises from 1 wt% to 60 wt% 2,2,4,4-tetramethylcyclobutane-1,3-dione, based on the total weight of the 2,2,4,4-tetramethylcyclobutane-1,3-dione and dimethylcyclohexanedicarboxylate.

10. The process according to claim 9, wherein the mixture of 2,2,4,4-tetramethylcyclobutane-1,3-dione and dimethylcyclohexanedicarboxylate comprises from 5 wt % to 50 wt % 2,2,4,4-tetramethylcyclobutane-1,3-dione, based on the total weight of the 2,2,4,4-tetramethylcyclobutane-1,3-dione and dimethylcyclohexanedicarboxylate.

11. The process according to claim 9, wherein the mixture of 2,2,4,4-tetramethylcyclobutane-1,3-dione and dimethylcyclohexanedicarboxylate comprises from 10 wt % to 25 wt % 2,2,4,4-tetramethylcyclobutane-1,3-dione, based on the total weight of the 2,2,4,4-tetramethylcyclobutane-1,3-dione and dimethylcyclohexanedicarboxylate.

12. The process according to claim 9, wherein the cyclohexanedicarboxylate is chosen from dimethylcyclohexane-1,2-dicarboxylate, diemethylcyclohexane-1,3-dicarboxylate, dimethylcyclohexane-1,4-dicarboxylate, and mixtures thereof.

13. The process according to claim 9, wherein the cyclohexanedicarboxylate is dimethylcyclohexane-1,4-dicarboxylate.

14. The process according to claim 1, wherein at least a portion of the 2,2,4,4-tetramethylcyclobutane-1,3-diol and at least a portion of the cyclohexanedimethanol are separated from the crude product to form a depleted product stream.

15. The process according to claim 14, wherein the depleted product stream is recycled to the mixture comprising 2,2,4,4-tetramethylcyclobutane-1,3-dione and dimethylcyclohexanedicarboxylate.

16. A process comprising
  (1) feeding isobutyric anhydride to a pyrolysis zone to produce a vapor effluent comprising dimethylketene, isobutyric acid and unreacted isobutyric anhydride;
  (2) cooling the vapor effluent to condense isobutyric acid and isobutyric anhydride and separating the condensate from the dimethylketene vapor;
  (3) feeding the dimethylketene vapor to an absorption zone wherein the dimethylketene vapor is dissolved in a dimethylcyclohexanedicarboxylate to produce an effluent comprising a solution of dimethylketene in the dimethylcyclohexanedicarboxylate;
  (4) feeding the absorption zone effluent to a dimerization zone wherein the effluent is heated to convert dimethylketene to 2,2,4,4-tetramethylcyclobutane-1,3-dione to produce an effluent comprising a solution of 2,2,4,4-tetramethylcyclobutane-1,3-dione in the dimethylcyclohexanedicarboxylate; and
  (5) contacting the 2,2,4,4-tetramethylcyclobutane-1,3-dione and dimethylcyclohexanedicarboxylate with hydrogen in the presence of a copper-based catalyst under conditions of temperature ranciinci from about 170 to about 210° C. and pressure ranging from about 2000 to about 6000 psig to yield about 25 wt % of 2,2,4,4-tetramethylcyclobutane-1,3-diol and about 30 wt % of cyclohexanedimethanol.

17. The process according to claim 16, wherein the dimethylcyclohexanedicarboxylate is chosen from dimethylcyclohexane-1,2-dicarboxylate, dimethylcyclohexane-1,3-dicarboxylate, dimethylcyclohexane-1,4-dicarboxylate, and mixtures thereof.

18. The process according to claim 16, wherein the dimethylcyclohexane-dicarboxylate comprises dimethylcyclohexane-1,4-dicarboxylate.

19. The process according to claim 16, wherein the catalyst comprises a copper chromite catalyst.

20. A process for the co-production of 2,2,4,4-tetramethylcyclobutane-1,3-diol and a second diol comprising contacting a mixture comprising 2,2,4,4-tetramethylcyclobutane-1,3-dione and reactive solvent with a copper-based catalyst in the presence of hydrogen under conditions of pressure ranging from about 2000 to about 6000 psig and temperature ranging from about 170 to about 210° C. to yield at least about 25 wt % of the 2,2,4,4-tetramethylcyclobutane-1,3-dione into 2,2,4,4-tetramethylcyclobutane-1,3-diol and at least about 30 wt % of the reactive solvent into the second diol.

21. The process according to claim 20, wherein the reactive solvent comprises a dimethylcyclohexanedicarboxylate chosen from dimethylcyclohexane-1,2-dicarboxylate, dimethylcyclohexane-1,3-dicarboxylate, dimethylcyclohexane-1,4-dicarboxylate, and mixtures thereof.

22. The process according to claim 20, wherein the reactive solvent comprises dimethylcyclohexane-1,4-dicarboxylate.

23. The process according to claim 20, wherein the catalyst comprises a copper chromite catalyst.

24. The process according to claim 1, wherein the yield of 2,2,4,4-tetramethylcyclobutane-1,3-diol is greater than about 20 wt % and the yield of the cyclohexanedimethanol is greater than about 30 wt %.

25. The process according to claim 1, wherein the ratio of cis to trans 2,2,4,4-tetramethylcyclobutane-1,3-diol is greater than about 0.75 and the ratio of cis to trans cyclohexanedimethanol is greater than about 1.10.

26. The process according to claim 24, wherein the ratio of cis to trans 2,2,4,4-tetramethylcyclobutane-1,3-diol is greater than about 0.75 and the ratio of cis to trans cyclohexanedimethanol is greater than about 1.10.

* * * * *

UNITED STATES PATENT AND TRADEMARK OFFICE
CERTIFICATE OF CORRECTION

PATENT NO. : 7,723,551 B2  Page 1 of 1
APPLICATION NO. : 11/948032
DATED : May 25, 2010
INVENTOR(S) : McCusker-Orth et al.

It is certified that error appears in the above-identified patent and that said Letters Patent is hereby corrected as shown below:

Column 17, Line 22, Claim 1 "ranciinci" should read --ranging--.

Column 18, Line 51, Claim 16 (5) "ranciinci" should read --ranging--.

Signed and Sealed this

Third Day of August, 2010

David J. Kappos
*Director of the United States Patent and Trademark Office*